United States Patent [19]

Grady

[11] Patent Number: 4,997,055

[45] Date of Patent: Mar. 5, 1991

[54] MULTIPLE CHANNEL STETHOSCOPE

[76] Inventor: Daniel J. Grady, 305 Yadkin Rd., Southern Pines, N.C. 28387

[21] Appl. No.: 512,343

[22] Filed: Apr. 23, 1990

[51] Int. Cl.$^5$ .................................................. A61B 7/02
[52] U.S. Cl. ....................................... 181/131; 181/137
[58] Field of Search ......................... 181/131, 135, 137

[56] References Cited

U.S. PATENT DOCUMENTS

| | | | |
|---|---|---|---|
| 1,847,607 | 3/1932 | Hardt | 181/131 |
| 1,853,951 | 4/1932 | Zala | 181/131 |
| 2,209,164 | 7/1940 | Kerr | 181/131 |
| 2,722,989 | 11/1955 | Tynan | 181/131 |
| 3,124,211 | 3/1964 | Cefaly | 181/131 |
| 3,144,091 | 8/1964 | Bodenger | 181/137 |
| 4,401,125 | 8/1983 | Taylor et al. | 181/131 X |
| 4,706,777 | 11/1987 | Baumberg | 181/137 |

Primary Examiner—Benjamin R. Fuller
Attorney, Agent, or Firm—Rhodes, Coats & Bennett

[57] ABSTRACT

The present invention is a stethoscope which provides the user with continuous access to physiologic sounds. The stethoscope consists of multiple, lightweight, disposable sound receiving sensors and shutoff valves which allow selective auscultation of specific sites without patient disturbance. In addition, depending upon the positions of the shutoff valves, the stethoscope may enhance sound conduction by producing constructive interference of sound waves. A means of attaching the sound receiving sensors to the skin is also described. Because the sound receiving sensors are disposable, the risk of infection due to cross-examination is minimized. Therefore, this invention is safer than known stethoscopes.

7 Claims, 3 Drawing Sheets

MULTIPLE CHANNEL STETHOSCOPE

FIELD OF INVENTION

This invention relates to medical equipment and apparatuses. More specifically, the invention relates to a stethoscope.

BACKGROUND OF THE INVENTION

Existing stethoscopes are currently utilized to auscultate or listen to physiologic sounds within the body. Auscultation with existing stethoscopes is currently performed by intermittently applying a stethoscope to the body surface through which the clinician hears various sounds. Intermittent auscultation may be a relatively benign procedure. However, several disadvantages and hazards are associated with the use of existing stethoscopes. First, patients undergoing surgery may have the sterile field invaded thereby risking infection in order for the clinician to auscultate the chest. Another disadvantage of known stethoscopes is that patients are frequently awakened and disturbed so that the clinician may apply a cold stethoscope to the patient's chest to monitor vital signs. Recent studies have shown serious developmental abnormalities in newborn infants who are frequently disturbed to auscultate heart and lung sounds with known stethoscopes. Another disadvantage of existing stethoscopes is that the quality of sound wave transmission is dependent upon an airtight seal between the stethoscope and the skin. In the absence of an airtight seal, background noise is inadvertently detected and physiologic sound transmission is impaired. Finally, another disadvantage of existing stethoscopes is that they are not capable of generating positive or constructive interference of physiologic sound waves.

Stethoscopes are known which use two sound receiving heads but have several disadvantages. The stethoscope shown in U.S. Pat. No. 4,706,777 to Baumberg discloses a stethoscope with two sound transmitting tubes connected to a valve. Depending upon the position of the valve, the clinician receives either mono or stereo sounds. However, even when receiving stereo sounds, the sound picked up by each sensor is transmitted through separate channels. In contrast, the present invention transmits sounds through a common tube with constructive interference of sound waves resulting.

Other patents show stethoscopes with multiple heads. In the Patents to Cefaly (U.S. Pat. No. 3,124,211) and Tynan (U.S. Pat. No. 2,722,989), the sound receiving heads are not capable of being used simultaneously. In the patents to Zala (U.S. Pat. No. 1,853,951), Bodenger (U.S. Pat. No. 3,144,091) and Hardt (U.S. Pat. No. 1,847,607), the sound receiving heads transmit sounds through separate tubes.

Finally, the Patent to Tailor et al. (U.S. Pat. No. 4,401,125) discloses a stethoscope securing pad which includes an adhesive surface for securing the head of the stethoscope to the patient's skin. However, this pad is larger than the diaphragm head and has only one adhesive surface. Also, it does not appear to form an airtight seal between the stethoscope head and the skin.

SUMMARY AND OBJECTS OF THE INVENTION

The present invention provides the clinician with a means of continuous access to a patient's physiologic sounds without disturbing the patient. A means of continuous access to these sounds is accomplished by attaching multiple, lightweight, disposable sound receiving sensors to the patient's skin using a double-sided adhesive ring. The multiple sound receiving heads connect to individual sound transmitting tubes and shutoff valves which merge into a common tube.

The present invention is superior to existing stethoscopes for several reasons. First, continuous attachment of lightweight sound receiving sensors to the chest avoids disturbing patients when frequent auscultation is necessary. Second, the use of a double-sided adhesive ring to attach the sound receiving sensors to the chest creates an airtight seal, thereby improving sound conduction. With known stethoscopes, the absence of an airtight seal is the most common problem encountered during auscultation. Third, the use of disposable sound receiving heads minimizes the risk of infection due to cross-contamination. Fourth, the use of multiple sound receiving heads with individual shutoff valves allows selective access to auscultation sites. Last, the unexpected discovery of positive sound wave interference resulting from the merging of multiple sound waves within a common transmitting tube makes this invention superior to previously known stethoscopes.

Other objects and advantages of the present invention will become apparent and obvious from a study of the following description and the accompanying drawings which are merely illustrative of such invention.

BRIEF DESCRIPTION OF THE DRAWINGS

FIG. 2-B is a section view of the shutoff valve housing showing the right shutoff valve in an open position with the left shutoff valve in a closed position.

FIG. 2-C is a section view of the shutoff valve housing showing the right shutoff valve in a closed position and the left shutoff valve in an open position.

FIG. 2-D is a section view of the shutoff valve housing both the right and left valves in open positions.

DETAILED DESCRIPTION

Figure 1:
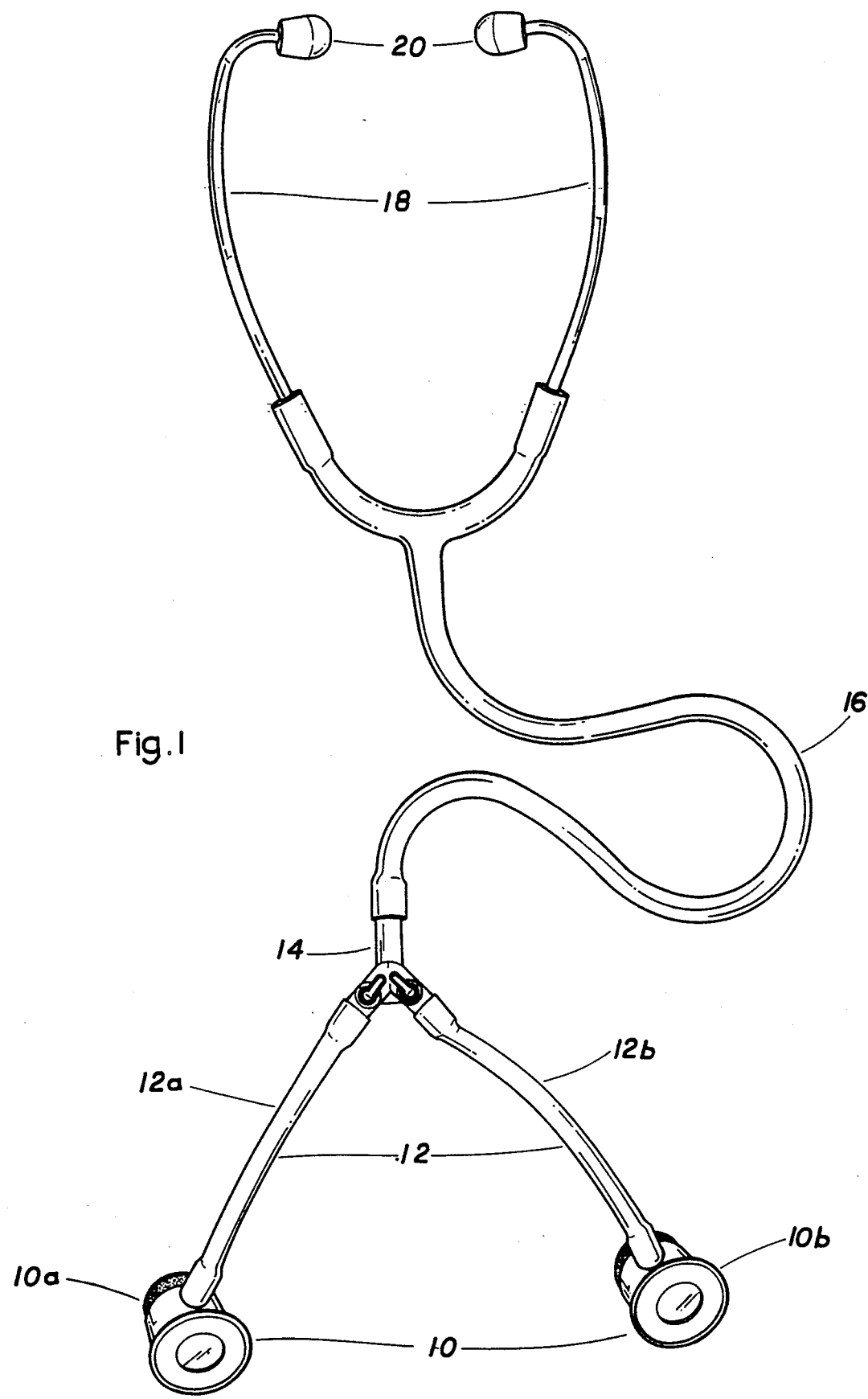
FIG. 1 is a plan view of a multiple channel stethoscope of the present invention.

FIG. 1 shows a multiple channel stethoscope with two sound receiving sensors 10 which are connected to individual sound conduction tubes 12. The left sound receiving sensor 10b connects to the left sound conducting tube 12b and the right sound receiving sensor 10a connects to the right sound conducting tube 12a via plastic connectors. Both the left sound conducting tube 12b and the right sound conducting tube 12a connect to the multiple channel shutoff valve housing unit shown generally at 14. The multiple channel shutoff valve housing unit 14 connects to a commoon shound conduction tube 16. The common sound conduction tube 16 connects to earpiece 18 and the earpiece 18 connect to eartips 20.

The sound receiving sensors 10 may be constructed from light-weight plastic or a combination of plastic and a lightweight metal such as aluminum. The sound conduction tubes and common tube may be made from plastic or rubber. The eartips, connectors, and multiple channel shutoff valve housing unit may be made of plastic.

Figure 2A:
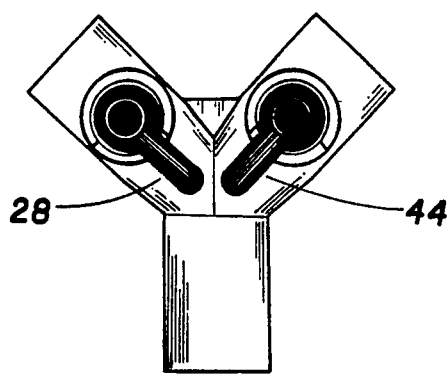
FIG. 2-A is an enlarged plan view of the multiple channel shutoff valve housing.
Figure 2B:
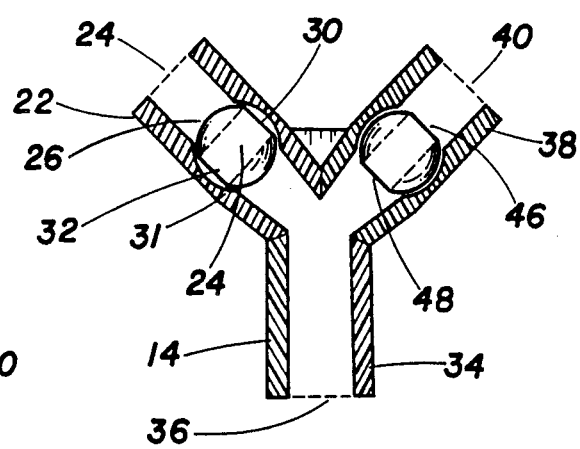
Figure 2C:
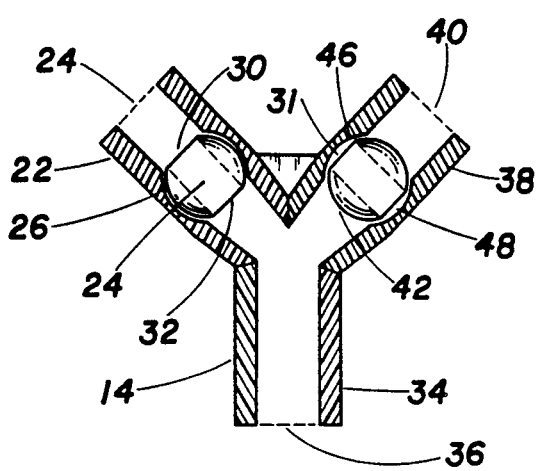
Figure 2D:
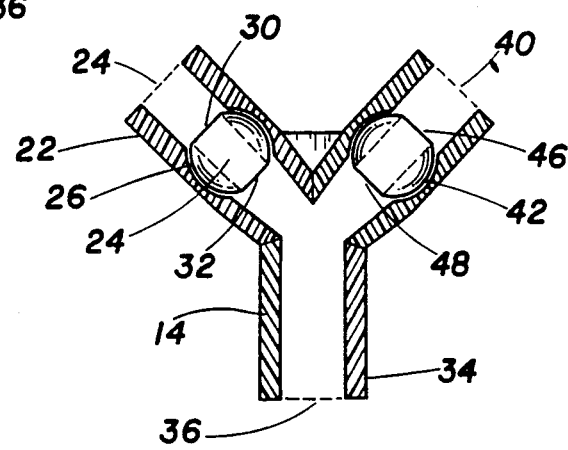

Referring to FIGS. 2A through 2D show the multiple channel shutoff valve housing 14 in more detail. FIG. 2A shows the left shutoff valve lever 28 which is directly connected to the left shutoff valve 26 (not shown in FIG. 2-A). The left shutoff valve lever 28 adjusts the position of the left shutoff valve 26. The right shutoff valve lever 44 is connected to the right shutoff valve 42 (not shown in FIG. 2-A). The shutoff valves 24 and 42 are located within the valve housing 14 as shown in FIGS. 2B through 2D. The valve levers 28 and 44 are mounted externally on the valve housing 14. Rotation of the valve levers 28 and 44 change the position of the shutoff valves 26 and 42 thereby opening or closing the valves.

FIGS. 2B, 2C, and 2D show enlarged, cross-sectional views of the shutoff valve housing unit 14. Reference will be made to these drawings in describing the operation of the invention.

Figure 3:
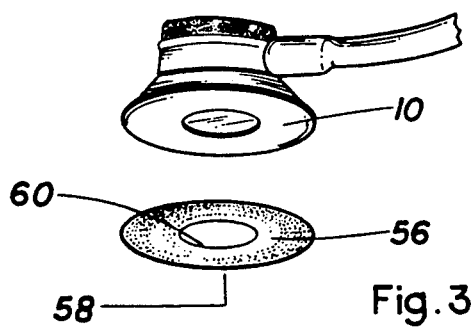
FIG. 3 is a perspective view showing how the sound receiving sensors are attaching to the skin using double-sided adhesive ring.

FIG. 3 shows a means of attaching the sound receiving sensors to the patient's skin using a double-sided, doughnut-shaped, adhesive ring indicated generally at 62. One side of the adhesive surface 56 attaches to the surface of the sound receiving sensor 10, while the opposite adhesive surface 58 attaches to the skin. The opening 60 in the adhesive ring allows physiologic sounds to be transmitted to the sound receiving sensor. The adhesive ring may be constructed from plastic and adhesive which is non-toxic and non-irritating to skin.

Following attachment of the sound receiving sensors 10a and 10b to the skin, the eartips 20 are inserted into the clinician's ears. Selective access to sound from a particular sound receiving sensor is achieved by rotation of the shutoff valve levers 28 and 44 with subsequent changes in position of the shutoff valves 26 and 42.

Right Sensor Access: FIG. 2-B shows the position of the shutoff valves 26 and 42 in order to auscultate sounds through the right sound receiving sensor 10a. The right shutoff valve 42 is rotated into an open position by adjusting the right shutoff valve lever 44 such that the right shutoff valve opening 46 communicates with the conducting tube connector lumen 40 and the common tube lumen 36. The left shutoff valve 26 is adjusted to a closed position by rotation of the left shutoff valve lever 28. Rotation of the left shutoff valve lever 28 causes the left shutoff valve opening to the conducting tube 30 to close and become seated against the inner wall of the valve housing 31. Simultaneously, the left shutoff valve opening to the common tube 32 is seated against the inner wall of the valve housing 31 thereby preventing sound conduction through the left valve.

Left Sensor Access: FIG. 2-C shows an enlarged, cross-sectional view of the shutoff valves when access to sounds from the left sensor is desired. The left valve lever 28 lever 28 (not shown in FIG. 2-C) is rotated to cause the left shutoff valve opening to the conducting tube 30 to communicate with the left conducting tube connector lumen 24. The left valve opening to the common tube 32 is allowed to communicate with the common tube lumen 36 in this valve position. To close the right valve 42, the right shutoff valve lever 44 is rotated to cause the right shutoff valve opening to the conducting tube 46 to seat against the inner wall of the valve housing 31. Also, in this position, the right shutoff valve opening to the common tube 48 is seated against the inner wall of the valve housing 31, thereby preventing sound transmission through the right valve.

Constructive Interference: FIG. 2-D shows an enlarged cross-sectional view of the shutoff valve positions when the invention may be used to create positive or constructive interference of sound waves. Both the right sound receiving sensor 10a and the left sound receiving sensor 10b are attached proximal to the same physiologic sound source. The right valve lever 44 is rotated to open the right shutoff valve 42 and the left shutoff valve lever 28 is rotated to open the left shutoff valve 26. In these positions, sound waves are conducted independently through both the right sound receiving sensor 10a and left sound receiving sensor 10b. In the common tube constructive or positive interference of sound waves occurs as sound waves from both the right and left sensors combine and interact. The interfering sound waves are transmitted through the common tube 16, through both earpiece 18, and through both eartips 20. The constructive inference of the sound waves was unexpectedly found to improve overall sound quality.

Figure 4:
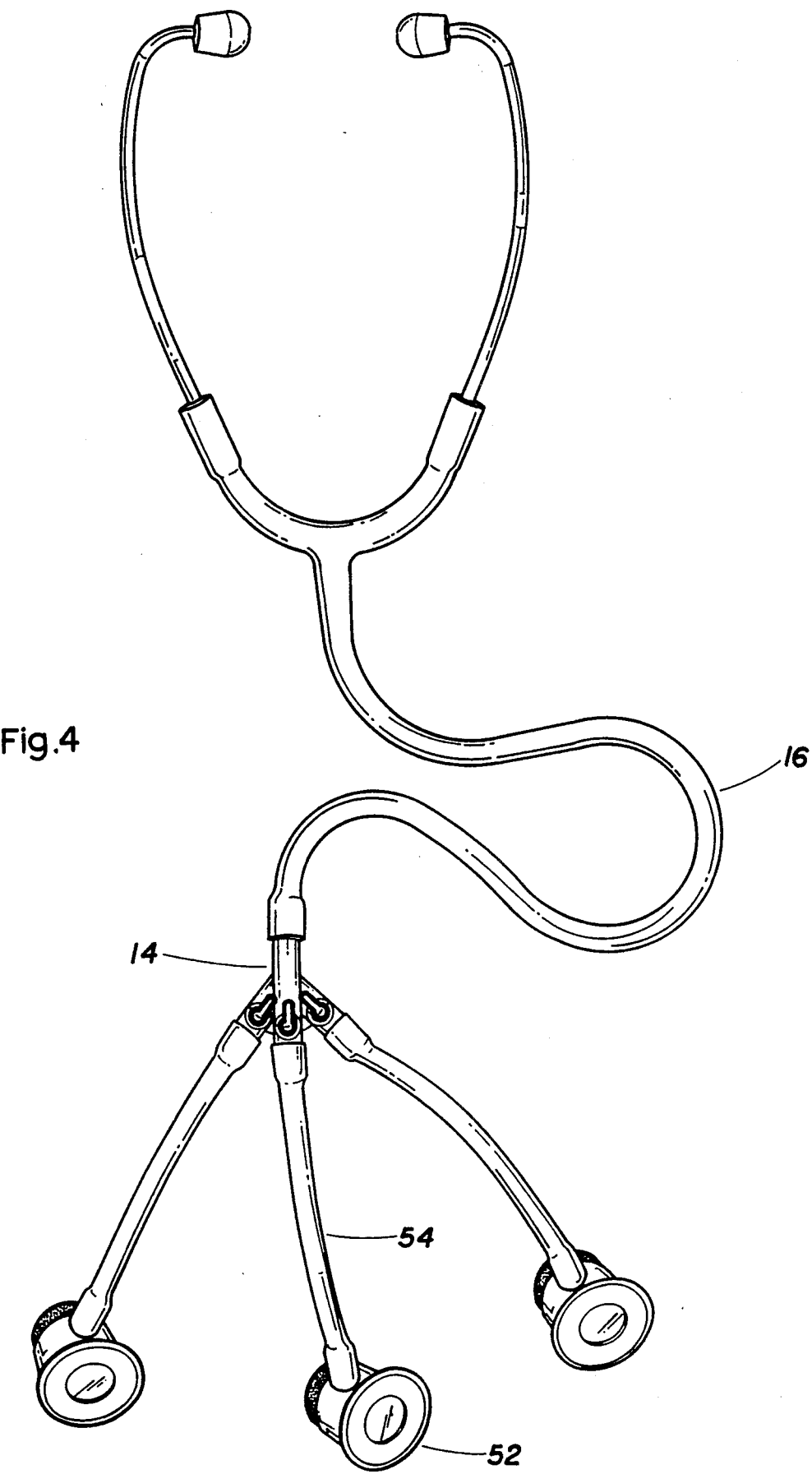
FIG. 4 is a view showing a second embodiment of the invention with three sound receiving sensors.

While the above description contains many specificities, these should not be construed as limitations on the scope of the invention, but rather as an exemplification of one preferred embodiment thereof. Many other variations are possible, such as utilizing different types of valves to open or occlude the sound conduction tubes. Also, as shown in FIG. 4, an additional sound receiving sensor 52, conducting tube 54, and shutoff valve may be constructed for continuous access to heart sounds (via the center sensor) and both lungs (via the right and left sensors).

The present invention may, of course, be carried out in other specific ways than those herein set forth without parting from the spirit and essential characteristics of the invention. The present embodiments are, therefore, to be considered as in all respects as illustrative and not restrictive and all changes coming within the meaning and equivalency range of the appended Claims are intended to be embraced therein.

What is claimed is:

1. A multi-channel stethoscope comprising:
   (a) at least two sound receiving sensors;
   (b) a pair of ear pieces adapted to be applied to respective ears of an examining person; and
   (c) a sound transmitting network for transmitting sound from said sound receiving sensors, to said earpieces, said sound transmitting network comprising:
      (1) a pair of initial sound conducting tubes communicatively connected to respective sound receiving sensors;
      (2) a common intermediate sound conducting tube communicatively connected to each of said initial sound conducting tubes; and
      (3) a pair of final sound conducting tubes each of which is communicatively connected at one end to said intermediate sound conducting tube and at an opposite end to respective ear pieces;
      (4) wherein said initial sound conducting tubes are of equal length so that sounds from respective sound receiving sensors merge in phase in said intermediate sound conducting tube and so that the sounds from respective sound receiving sensors reinforce each other to produce a unified sound of higher intensity.

2. The multi-channel stethoscope according to claim 1 further including valve means disposed between said initial sound conducting members and said intermediate sound conducting member for selectively blocking sounds from said sound receiving sensors.

3. The multi-channel stethoscope according to claim 2 wherein said valve means comprises a valve housing unit having a plurality of valves, each of which is formed with a sound conducting passage, said valve being movable between an open position wherein sounds are transmitted through said sound conducting passage in said valve and a closed position in which sounds are blocked by said valve.

4. The multi-channel stethoscope according to claim 1 further including means for attaching said sound receiving sensors to a body of a patient.

5. The multi-channel stethoscope according to claim 4 wherein said attaching means includes an adhesive ring having a central opening formed therein, said adhesive ring having a first surface adapted to attach to the sound receiving sensor and a second surface adapted to attach to the body of the patient, wherein both said first and second surfaces are coated with an adhesive.

6. The multi-channel stethoscope according to claim 5 wherein said adhesive ring provides an airtight seal between the body of the patient and the sound receiving sensors.

7. The multi-channel stethoscope according to claim 1 wherein said sound conducting members are tubular members.

* * * * *